United States Patent [19]

Parish

[11] Patent Number: 5,087,268
[45] Date of Patent: Feb. 11, 1992

[54] PROCESSES FOR PRODUCING A FERROUS PICRATE FUEL ADDITIVE

[76] Inventor: Walter W. Parish, 145 North Geneva Rd., Orem, Utah 84057

[21] Appl. No.: 686,819

[22] Filed: Apr. 17, 1991

[51] Int. Cl.$^5$ .................. C10L 9/10; C07F 15/02
[52] U.S. Cl. .................. 44/312; 44/367; 44/413; 556/138; 556/150
[58] Field of Search .................. 44/367, 413, 312; 556/150, 138

[56] References Cited

U.S. PATENT DOCUMENTS

| | | | |
|---|---|---|---|
| 4,073,626 | 2/1978 | Simmons | 44/367 |
| 4,099,930 | 7/1978 | Webb | 44/354 |
| 4,424,063 | 1/1984 | Hart | 44/321 |

Primary Examiner—Prince Willis, Jr.
Assistant Examiner—Thomas Steinberg
Attorney, Agent, or Firm—Olson & Hoggan

[57] ABSTRACT

A process for producing an additive for hydrocarbon fuels by combining picric acid, powdered iron, an activating acid, and a liquid organic solvent. Alternatively, the powdered iron can first be washed with the activating acid and the rinsed with water or alcohol or water followed by alcohol; subsequently the washed and rinsed iron is combined with the picric acid and the liquid organic solvent. In the case of either alternative, hydroquinone can be added to the mixture in order to control undesired oxidation and corrosion, thereby further enhancing the stability of the additive.

58 Claims, No Drawings

PROCESSES FOR PRODUCING A FERROUS PICRATE FUEL ADDITIVE

BACKGROUND OF THE INVENTION

1. Field of the Invention

This invention relates to processes for producing a fuel additive composition.

2. Description of the Related Art

In U.S. Pat. No. 2,506,539 Mr. Harold Boardman claimed, inter alia, "[a]s an addition agent for gasoline, a mixture of one part by weight of ferrous picrate and about 44 parts by weight of picric acid dissolved in a mixture of methylated spirits and benzene." The disclosure identifies the methylated spirits as grain alcohol, denatured through the addition of a small percentage of wood alcohol, and nine volumes of benzene; observes that the methylated spirits could be replaced with methanol, ethanol, propanol, or mixtures of lower fatty alcohols; and remarks that substitutes for the benzene include toluene. Unfortunately, benzene is toxic; and methylated spirits attack the metallic containers which usually enclose gasoline. The production of this additive creates, moreover, substantial quantities of picratecontaminated barium sulfate waste and exposes those preparing the additive to hazardous barium picrate, ferrous picrate, and other barium and picrate residues.

Richard W. Simmons in U.S. Pat. No. 3,282,858 claimed an improved process for producing the additive, which mainly consists of reacting ferrous sulfate with sodium carbonate in water, removing the precipitated ferrous carbonate, pouring alcohol on the precipitate, adding hydroquinone and picric acid to the resultant alcoholic suspension, drawing alcohol off the ferrous picrate crystals which have then formed, placing these crystals in fusel oil, mixing this solution with a nonoxidizing hydrocarbon solvent in which picric acid has been dissolved, and then adding silica gel. This process is said to be safer since it eliminates dealing with highly hazardous dry ferrous picrate. But it still involves a lengthy process of synthesizing, isolating, and purifying ferrous picrate. Additionally, it generates alcohol waste contaminated with ferrous picrate as well as silica gel waste containing ferrous picrate and picric acid.

In the disclosure for his U.S. Pat. No. 4,073,626, Richard W. Simmons noted that his first patent had, inter alia, reduced the corrosiveness of the Boardman patent by replacing the benzene and that the Boardman additive was unstable. The preferable nitro acid salt in the composition claimed within this second patent by Simmons is ferrous picrate. Although no process is claimed, one example is given for the production of the additive. This example closely follows the process in Simmons's prior patent to the point just prior to alcohol being drawn off the ferrous picrate. Then, instead of removing the alcohol, placing the ferrous picrate crystals in fusel oil, and mixing this solution with a non-oxidizing hydrocarbon solvent in which picric acid has been dissolved, the solution resulting from the ferrous carbonate, picric acid, and isopropyl alcohol simply had 1-nitropropane added to it and was subsequently dissolved in a mixture of isopropyl alcohol and Pacific base oil. Although no isolation and purification of the ferrous picrate was performed, the process is still lengthy and produces alcohol waste.

All claims in the three U.S. Pat. Nos. of Harry Matthew Webb—No. 4,099,930; No. 4,129,421; and No. 4,265,639—involve ferrous sulfate and water, which create an undesirable instability in the additive, increase corrosivity, and limit compatibility of the additive with hydrocarbon fuels. (This is explicit for all claims except numbers 5 and 6 of U.S. Pat. No. 4,099,930, where ferrous sulfate is expressly enumerated as an ingredient but water is not; still, the disclosure for U.S. Pat. No. 4,099,930 indicates that water would be included.)

To solve the problem with instability Myndert T. Scholtz in U.S. Pat. No. 4,265,639 uses EDTA to form an iron (II)/EDTA chelate with all of the +2 iron in the additive and a sufficient amount of an amine to form a picric acid/amine complex with essentially all of the picric acid in the additive. Examples within the disclosure show the source of the +2 iron as being hydrated ferrous sulfate, although the claims are not so limited.

The final patent in this series—U.S. Pat. No. 4,424,063—is a rather unique patent. Most notably, it appears to contain composition of matter claims which do not specify the nature of the composition, but merely state the ingredients utilized to manufacture such composition. The principal disadvantage of the process disclosed, by means of example, for creating this composition is the lengthy period, i.e., twenty-four hours, which the process requires.

SUMMARY OF THE INVENTION

The instant invention solves the problems of the hazardous nature of solid ferrous picrate as well as the time and expense of isolating and purifying ferrous picrate by producing the ferrous picrate in situ within the solution which will, itself, become the additive. Of course, this also minimizes the production of hazardous wastes since no intermediate products are formed.

And the instability is eliminated through the development of a process that requires neither sulfates nor water.

It appears, however, that the process disclosed by U.S. Pat. No. 4,424,063 possesses these same positive attributes. But the process of the instant invention is capable of rapidly—within only a few minutes—producing the desired fuel additive composition whereas U.S. Pat. No. 4,424,063 states, as noted above, that twenty-four hours is consumed by its process.

DETAILED DESCRIPTION

Numerous patents have been granted for processes which utilize picric acid, some form of iron, and a solvent to produce an additive for hydrocarbon fuels which increases the efficiency of the combustion of such fuels, resulting in better mileage, reduced deposits within the engine, and a smaller quantity of pollutants in the exhaust.

The first such patent, U.S. Pat. No. 2,506,539, was granted to Mr. Harold Boardman. This was followed by two patents for Richard W. Simmons—U.S. Pat. No. 3,282,858 and U.S. Pat. No. 4,073,626. Then Mr. Harry Matthew Webb received three patents—U.S. Pat. No. 4,099,930; U.S. Pat. No. 4,145,190; and U.S. Pat. No. 4,265,639. Subsequently, U.S. Pat. No. 4,265,639 was awarded to Mr. Myndert T. Scholtz. And the most recent patent in this series—U.S. Pat. No. 4,424,063—was awarded to Mr. Rien 'T Hart.

The Boardman additive unfortunately contains benzene, a toxic substance, and methylated spirits, which attack the metallic containers that are most frequently utilized to contain gasoline. Its production also generates substantial hazardous waste.

The first Richard W. Simmons U.S. Pat. No. 3,282,858, eliminated the benzene and the danger of compelling those who prepare the additive to utilize dry ferrous picrate, which is highly flammable. But the process of this patent still produces considerable hazardous waste and continues to require a lengthy process of synthesizing, isolating, and purifying ferrous picrate. And all subsequently patented compositions except the most recent, i.e., the composition which is the subject of U.S. Pat. No. 4,424,063, have utilized ferrous sulfate and water which, as noted above, create an undesirable instability in the additive, increase corrosivity, and limit compatibility of the additive with hydrocarbon fuels.

U.S. Pat. No. 4,424,063, did, as does the instant invention, solve the problems of isolating and purifying ferrous picrate and generating hazardous wastes, by producing the ferrous picrate in situ within the solution which will, itself, become the additive. And the instability of the additive is eliminated, in the processes of both U.S. Pat. No. 4,424,063 and the instant invention, by utilizing methods which require neither sulfates nor water.

The disclosure for U.S. Pat. No. 4,424,063 indicates, though, that the process for making the patented composition consumes twenty-four hours. And the instant invention can produce the additive in less than ten minutes—a decided industrial and economic advantage within the commercial realm.

The instant process simply combines and agitates (during and subsequent to the combining) powdered elemental iron—the least expensive form of iron—with picric acid, a liquid organic solvent, and an activating acid. The key ingredient for accelerating the production of the additive is the activating acid which reacts with the surface of the iron to remove any substances therefrom and thereby to expose (or activate) a surface of pure iron.

The activating acid can be hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, or senecioic acid. Sulfuric, phosphoric, heptananoic, octanoic, Myristic, phenylacetic, 2-naphylacetic, and tartaric acid were almost completely ineffective for activating the iron; and nitric acid caused instability in the additive.

A rather broad range for the concentration of activating acid is feasible. Depending upon the particular activating acid selected, it may constitute from 20 percent to 0.01 percent (by weight) of the additive. The preferred range is, however, 1 percent to 0.1 percent.

The liquid organic solvent can be a mixture of a hydrocarbon distillate and an alcohol. Toluene, benzene, ortho-xylene, meta-xylene, para-xylene, 150 solvent, petroleum naphtha, or mineral spirits can be the hydrocarbon distillate. Acceptable alcohols are isopropyl, butanol, propanol, octanol, and ethyl hexanol.

However, any of the common classes of organic solvents are suitable provided they are compatible with the ferrous iron and excess picric acid which exist in the additive. Such solvents may be utilized individually or mixed with solvents from the same or other classes.

Suitable classes of solvents and representative examples of each class are the following:

aliphatic hydrocarbons—alkanes (pentanes through nonanes), VM & P Naphtha, 360 Solvent, Mineral Spirits, Stoddard Solvent, 140 Solvent, 460 Solvent, mineral seal oil, mineral oil, kerosene, and other aliphatic petroleum distillate fractions;

aromatic hydrocarbons—benzene, toluene, xylenes, ethyl benzene, SC Solvents, H.A.N. Solvent, and other aromatic-containing petroleum distillate fractions;

alcohols—cyclic, branched, and straight chain alkanols through $C_{10}$ including methanol, ethanol, propanol, isopropanol, butanols, octanols, ethylhexanol, and cyclohexanol;

glycols—ethylene glycol, propylene glycol, diethylene glycol, dipropylene glycol, triethylene glycol, tripropylene glycol, tetraethylene glycol, and glycerine;

aliphatic esters—ethyl formate, ethyl acetate, propyl acetates, butyl acetates, amyl acetates, isobutyl isobutyrate, other esters of lower alcohols through $C_{10}$ with lower acids through $C_{10}$, and glycol ether acetates;

aromatic esters—ethyl benzoate and phthalate esters;

aliphatic ketones—cyclic, branched, and straight chain aliphatic ketones through $C_{10}$ such as acetone, methyl ethyl ketone, methyl isobutyl ketone, cyclohexanone, diisobutyl ketone, methyl isoamyl ketone, and isophorone;

aromatic ketones—acetophenone and propiophenone;

aliphatic ethers—cyclic, branched, and straight chain aliphatic ethers through $C_{10}$ such as ethyl ether, methyl tert-butyl ether, ethyl tert-butyl ether, diisopropyl ether, dibutyl ether, tetrahydrofuran, dioxane, various gylcol ethers (such as ethylene glycol ether, monomethyl glycol ether, diethylene glycol monoethyl ether, diethylene glycol monobutyl ether, propylene glycol monomethyl ether, dipropylene glycol monomethyl ether, and tripropylene glycol monomethyl ether), various glymes (such as monoglyme, diglyme, triglyme, and tetraglyme), and related glycol ethers of higher alcohols through $C_{10}$;

aromatic ethers—anisole, ethyl phenyl ether, and diphenyl ether;

amides—formamide, methyl formamide, dimethylformamide, dimethylacetamide, N-methylpyrrolidinone, and tetramethyl urea;

chlorinated alkanes—branched and straight chain chlorinated alkanes through $C_4$ such as methylene chloride, chloroform, carbon tetrachloride, 1,1,1-trichloroethane, 1,1,2-trichloroethane, ethylene dichloride, propylene dichloride, chloropropane, and chlorobutanes;

chlorinated alkenes—branched and straight chain chlorinated alkenes through $C_4$ such as trichloroethylene and perchloroethylene;

chlorinated aromatics—chlorobenzene, ortho dichlorobenzene, meta dichlorobenzene, para dichlorobenzene, and trichlorobenzenes;

nitro aliphatics—branched and straight chain nitro aliphatics through $C_3$ such as nitromethane, nitroethane, 1-nitropropanes, and 2-nitropropanes; and nitro aromatics—nitrobenzene, dinitrobenzenes, nitrotoluenes, and dinitrotoluenes.

The entire spectrum of ingredients for the additive can be combined in any order, although when toluene and isopropyl alcohol are utilized it is desirable first to add the picric acid to the toluene because picric acid is more soluble in toluene than it is in isopropyl alcohol. This is also true for liquid organic solvents which are mixtures of some other alcohols and hydrocarbon distillates.

Optionally, hydroquinone can be added to control undesired oxidation and corrosion, thereby, further enhancing the stability of the additive. The proportion of the ingredients can be determined from the prior art as well as the examples given below.

Ingredients can be added or altered within the instant process to create any of the compositions disclosed or claimed in any of the above-reference patents.

And an alternate exists to the instant process described above. Instead of adding the activating acid to the other ingredients, one can first wash the powdered elemental iron with the activating acid; second, rinse the iron with alcohol or water or water followed by alcohol; and then combine the washed and rinsed iron with the picric acid and the liquid organic solvent. The rinsing alcohol may be methanol, ethanol, propanol, or isopropyl alcohol.

Again, the order of combining liquid ingredients within this final step is not critical. And the addition of the hydroquinone is once more an option as is the use of additional or alternate ingredients to create any of the compositions disclosed or claimed in the above-referenced patents.

Examples of the two alternate processes using various acids (where "parts" refers to parts by weight) are:

EXAMPLE 1

A mixture of 85 parts toluene, 15 parts isopropyl alcohol, 1 part picric acid, 0.5 parts 12 N HCl, and 0.05 parts powdered elemental iron was agitated in a suitably sized reactor for 8 minutes to give an additive containing 100 ppm of iron.

EXAMPLE 2

A mixture of 85 parts toluene, 15 parts isopropyl alcohol, 1 part picric acid, 0.5 parts 70% perchloric acid, and 0.05 parts powdered elemental iron was agitated in a suitably sized reactor for 22 minutes to give an additive containing 400 ppm of iron.

3 EXAMPLE 3

A mixture of 85 parts toluene, 15 parts isopropyl alcohol, 1 part picric acid, 0.5 parts glycolic acid, 0.2 parts hydroquinone, and 0.05 parts powdered elemental iron was agitated for 2 hours in a suitably sized reactor to give an additive containing 100 ppm of iron.

EXAMPLE 4

A mixture of 85 parts toluene, 15 parts isopropyl alcohol, 1 part picric acid, 0.5 parts 98% formic acid, and 0.05 parts powdered elemental iron was agitated in a suitably sized reactor for 40 minutes to give an additive containing 100 ppm of iron. The same mixture when agitated for 1 hour and 15 minutes gave an additive containing 400 ppm of iron.

EXAMPLE 5

A mixture of 85 parts toluene, 15 parts isopropyl alcohol, 1 part picric acid, 0.5 parts propionic acid, 0.3 parts hydroquinone, and 0.05 parts powdered elemental iron was agitated in a suitably sized reactor for four hours and forty minutes to give an additive containing 100 ppm of iron.

EXAMPLE 6

A mixture of 75 parts 150 Solvent, 20 parts 2-ethylhexanol, 4.8 parts picric acid, 0.2 parts hydroquinone, and 0.04 parts powdered elemental iron (0.25 parts Ethylenediaminetetraacetic acid,) was agitated for 30 minutes to give a product containing 600 ppm of iron.

EXAMPLE 7

The activation of powdered elemental iron was conducted as follows: 2 parts of commercial powdered elemental iron was suspended in 10 parts of 12N hydrochloric acid for 1 minute then rapidly quenched with 90 parts of cold water. Agitation was discontinued, the iron was allowed to settle to the bottom of the container, and the liquid water and hydrochloric acid was drawn off. The powdered elemental iron was then resuspended in 100 parts of fresh water for 5 minutes, subsequently being allowed to settle and having the rinse water drawn off it. Finally, the iron was rinsed with 10 parts of methanol three times and stored under the last rinse until use. Immediately prior to use, the powdered elemental iron is removed by filtration. (Other acids may be substituted for 12N HCl and other solvents may be substituted for the water and methanol. Organic acids generally require activation times longer than 1 minute.)

EXAMPLE 8

A mixture of 80 parts toluene, 20 parts isopropyl alcohol, 5 parts picric acid, 0.2 parts hydroquinone, and 0.05 parts powdered elemental iron (previously washed with 6N HCl, then rinsed first with water and second with isopropyl alcohol) was agitated for approximately 45 minutes to give an additive containing 360 ppm of iron.

EXAMPLE 9

A mixture of 85 parts toluene, 15 parts isopropyl alcohol, 9 parts picric acid, and 0.05 parts powdered elemental iron (previously washed with 6N HCl, then rinsed first with water and second with isopropyl alcohol) was agitated for about 10 minutes to give an additive containing 360 ppm of iron.

EXAMPLE 10

A mixture of 990 parts acetone, 10 parts picric acid, and 1 part activated powdered elemental iron was agitated for 15 minutes to give an additive containing 481 ppm of iron. The same mixture when agitated for 30 minutes gave an additive containing 573 ppm of iron; when agitated for 1 hour, of 712 ppm.

And two striking examples of the effectiveness of the activating acid are as follows:

EXAMPLE 11

Enough powdered elemental iron to give an additive containing 684 ppm of iron was added to 1 part picric acid dissolved in 85 parts toluene and 15 parts isopropyl alcohol. After agitating the mixture for nearly 3 days the iron content of the solution was only 53 ppm and was showing no further increase. But when enough powdered elemental iron to produce an additive containing 965 ppm of iron was added to 1 part picric acid, 85 parts toluene, 15 parts isopropyl alcohol, and 0.5 parts of 12N HCl, agitation for less than four hours gave an additive containing 900 ppm of iron. A similar reaction with 0.5 parts of 70% perchloric acid gave an additive containing 900 ppm or iron after having been agitated 1 hour and 15 minutes.

EXAMPLE 12

A mixture of 2 parts of picric acid in 198 parts of toluene was divided into two portions. 0.1 part of commercial powdered elemental iron was added to each portion, and 0.1 part 90% formic acid was added to one portion. After nineteen hours of agitation, the portion containing formic acid gave a product containing 10 ppm of iron whereas the other portion only gave approximately 0.1 ppm of iron.

In the preferred embodiment the first step is the addition of 1 part picric acid to 85 parts toluene. To this mixture is then added 15 parts isopropyl alcohol, 0.5 parts 12 N hydrochloric acid, and 0.05 parts powdered elemental iron.

I claim:

1. A process to manufacture an additive for hydrocarbon fuels, which comprises:
   combining picric acid, powdered elemental iron, an activating acid, and a liquid organic solvent and
   agitating said picric acid, said powdered elemental iron, said activating acid, and said liquid organic solvent during and subsequent to said combining.

2. The process to manufacture an additive for hydrocarbon fuels as recited in claim 1, further comprising:
   combining hydroquinone with the other said ingredients; and
   agitating said hydroquinone and the other said ingredients during and subsequent to said combining.

3. The process to manufacture an additive for hydrocarbon fuels as recited in claim 1, wherein the liquid organic solvent comprises a mixture of:
   a hydrocarbon distillate selected from the group consisting of benzene, ortho-xylene, meta-xylene, para-xylene, 150 solvent, petroleum naphtha, and mineral spirits; and
   an alcohol selected from the group consisting of butanol, propanol, octanol, and ethyl hexanol.

4. The process to manufacture an additive for hydrocarbon fuels as recited in claim 3, further comprising:
   combining hydroquinone with the other said ingredients; and
   agitating said hydroquinone and the other said ingredients during and subsequent to said combining.

5. The process to manufacture an additive for hydrocarbon fuels as recited in claim 3, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

6. The process to manufacture an additive for hydrocarbon fuels as recited in claim 5, further comprising:
   combining hydroquinone with the other said ingredients; and
   agitating said hydroquinone and the other said ingredients during and subsequent to said combining.

7. The process to manufacture an additive for hydrocarbon fuels as recited in claim 1, wherein the liquid organic solvent is one or more solvents selected from the group consisting of aliphatic hydrocarbons, aromatic hydrocarbons, alcohols, glycols, aliphatic esters, aromatic esters, aliphatic ketones, aromatic ketones, aliphatic ethers, aromatic ethers, amides, chlorinated alkanes, chlorinated alkenes, chlorinated aromatics, nitro aliphatics, and nitro aromatics.

8. The process to manufacture an additive for hydrocarbon fuels as recited in claim 7, further comprising:
   combining hydroquinone with the other said ingredients; and
   agitating said hydroquinone and the other said ingredients during and subsequent to said combining.

9. The process to manufacture an additive for hydrocarbon fuels as recited in claim 7, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

10. The process to manufacture an additive for hydrocarbon fuels as recited in claim 9, further comprising:
    combining hydroquinone with the other said ingredients; and
    agitating said hydroquinone and the other said ingredients during and subsequent to said combining.

11. A process to manufacture an additive for hydrocarbon fuels, comprising:
    first, washing powdered elemental iron with an activating acid;
    second, rinsing said powdered elemental iron with a rinsing agent;
    third, combining said washed and rinsed powdered elemental iron with picric acid and a liquid organic solvent; and
    fourth, agitating said washed and rinsed powdered elemental iron, said picric acid, and said liquid organic solvent during and subsequent to said combining.

12. The process to manufacture an additive for hydrocarbon fuels as recited in claim 11, further comprising:
    combining hydroquinone with said washed and rinsed powdered elemental iron, said picric acid, and said liquid organic solvent; and
    agitating said hydroquinone, said washed and rinsed powdered elemental iron, said picric acid, and said liquid organic solvent both during and subsequent to said combining.

13. The process to manufacture an additive for hydrocarbon fuels as recited in claim 11, wherein:
    the rinsing agent is an alcohol selected from the group consisting of methanol, ethanol, propanol, and isopropyl alcohol; and
    the liquid organic solvent comprises a mixture of:
    a hydrocarbon distillate selected from the group consisting of benzene, ortho-xylene, metaxylene, para-xylene, 150 solvent, petroleum naphtha, and mineral spirits; and
    an alcohol selected from the group consisting of butanol, propanol, octanol, and ethyl hexanol.

14. The process to manufacture an additive for hydrocarbon fuels as recited in claim 13, further comprising:
    combining hydroquinone with said washed and rinsed powdered elemental iron, said picric acid, and said liquid organic solvent; and
    agitating said hydroquinone, said washed and rinsed powdered elemental iron, said picric acid, and said liquid organic solvent both during and subsequent to said combining.

15. The process to manufacture an additive for hydrocarbon fuels as recited in claim 13, wherein the activating acid is an acid selected the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

16. The process to manufacture an additive for hydrocarbon fuels as recited in claim 15, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

17. The process to manufacture an additive for hydrocarbon fuels as recited in claim 11, wherein:
the rinsing agent is an alcohol selected from the group consisting of methanol, ethanol, propanol, and isopropyl alcohol; and
the liquid organic solvent is one or more solvents selected from the group consisting of aliphatic hydrocarbons, aromatic hydrocarbons, alcohols, glycols, aliphatic esters, aromatic esters, aliphatic ketones, aromatic ketones, aliphatic ethers, aromatic ethers, amides, chlorinated alkanes, chlorinated alkenes, chlorinated aromatics, nitro aliphatics, and nitro aromatics.

18. The process to manufacture an additive for hydrocarbon fuels as recited in claim 17, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

19. The process to manufacture an additive for hydrocarbon fuels as recited in claim 17, wherein the activating acid is an acid selected the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

20. The process to manufacture an additive for hydrocarbon fuels as recited in claim 19, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

21. The process to manufacture an additive for hydrocarbon fuels as recited in claim 11, further comprising rinsing said powdered elemental iron with water after said powdered elemental iron has been washed with said activating acid but before said iron powder has been rinsed with said rinsing agent.

22. The process to manufacture an additive for hydrocarbon fuels as recited in claim 21, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

23. The process to manufacture an additive for hydrocarbon fuels as recited in claim 21, wherein:
the rinsing agent is an alcohol selected from the group consisting of methanol, ethanol, propanol, and isopropyl alcohol; and
the liquid organic solvent comprises a mixture of:
a hydrocarbon distillate selected from the group consisting of benzene, ortho-xylene, metaxylene, para-xylene, 150 solvent, petroleum naphtha, and mineral spirits; and
an alcohol selected from the group consisting of butanol, propanol, octanol, and ethyl hexanol.

24. The process to manufacture an additive for hydrocarbon fuels as recited in claim 23, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

25. The process to manufacture an additive for hydrocarbon fuels as recited in claim 23, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

26. The process to manufacture an additive for hydrocarbon fuels as recited in claim 25, further comprising:
combining hydroquinone with said washed and rinsed powdered elemental iron, said picric acid, and said liquid organic solvent; and
agitating said hydroquinone, said washed and rinsed powdered elemental iron, said picric acid, and said liquid organic solvent both during and subsequent to said combining.

27. The process to manufacture an additive for hydrocarbon fuels as recited in claim 21, wherein:
the rinsing agent is an alcohol selected from the group consisting of methanol, ethanol, propanol, and isopropyl alcohol; and
the liquid organic solvent is one or more solvents selected from the group consisting of aliphatic hydrocarbons, aromatic hydrocarbons, alcohols, glycols, aliphatic esters, aromatic esters, aliphatic ketones, aromatic ketones, aliphatic ethers, aromatic ethers, amides, chlorinated alkanes, chlorinated alkenes, chlorinated aromatics, nitro aliphatics, and nitro aromatics.

28. The process to manufacture an additive for hydrocarbon fuels as recited in claim 27, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

29. The process to manufacture an additive for hydrocarbon fuels as recited in claim 27, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

30. The process to manufacture an additive for hydrocarbon fuels as recited in claim 29, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

31. The process to manufacture an additive for hydrocarbon fuels as recited in claim 11, wherein:
   the rinsing agent is water; and
   the liquid organic solvent comprises a mixture of:
   a hydrocarbon distillate selected from the group consisting of benzene, ortho-xylene, metaxylene, paraxylene, 150 solvent, petroleum naphtha, and mineral spirits; and
   an alcohol selected from the group consisting of butanol, propanol, octanol, and ethyl hexanol.

32. The process to manufacture an additive for hydrocarbon fuels as recited in claim 31, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

33. The process to manufacture an additive for hydrocarbon fuels as recited in claim 31, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

34. The process to manufacture an additive for hydrocarbon fuels as recited in claim 33, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

35. The process to manufacture an additive for hydrocarbon fuels as recited in claim 11, wherein:
   the rinsing agent is water; and
   the liquid organic solvent is one or more solvents selected from the group consisting of aliphatic hydrocarbons, aromatic hydrocarbons, alcohols, glycols, aliphatic esters, aromatic esters, aliphatic ketones, aromatic ketones, aliphatic ethers, aromatic ethers, amides, chlorinated alkanes, chlorinated alkenes, chlorinated aromatics, nitro aliphatics, and nitro aromatics.

36. The process to manufacture an additive for hydrocarbon fuels as recited in claim 35, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

37. The process to manufacture an additive for hydrocarbon fuels as recited in claim 35, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

38. The process to manufacture an additive for hydrocarbon fuels as recited in claim 37, further comprising:
   combining hydroquinone with said washed and rinsed powdered elemental iron, said picric acid, and said liquid organic solvent; and
   agitating said hydroquinone, said washed and rinsed powdered elemental iron, said picric acid, and said liquid organic solvent both during and subsequent to said combining.

39. A process to manufacture an additive for hydrocarbon fuels, which comprises:
   combining picric acid, powdered elemental iron, toluene, isopropyl alcohol, and an activating acid; and
   agitating said picric acid, said powdered elemental iron, said toluene, said isopropyl alcohol, and said activating acid during and subsequent to said combining.

40. The process to manufacture an additive for hydrocarbon fuels as recited in claim 39, further comprising:
   combining hydroquinone with the other said ingredients; and
   agitating said hydroquinone and the other said ingredients during and subsequent to said combining.

41. The process to manufacture an additive for hydrocarbon fuels as recited in claim 39, wherein the activating acid is selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

42. The process to manufacture an additive for hydrocarbon fuels as recited in claim 41, further comprising:

combining hydroquinone with the other said ingredients; and agitating said hydroquinone and the other said ingredients during and subsequent to said combining.

43. A process to manufacture an additive for hydrocarbon fuels, comprising:

first, washing powdered elemental iron with an activating acid;

second, rinsing said powdered elemental iron with a rinsing agent;

third, combining said washed and rinsed powdered elemental iron with picric acid, toluene, and isopropyl alcohol; and fourth, agitating said washed and rinsed powdered elemental iron, said picric acid, said toluene, and said isopropyl alcohol during and subsequent to said combining.

44. The process to manufacture an additive for hydrocarbon fuels as recited in claim 43, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

45. The process to manufacture an additive for hydrocarbon fuels as recited in claim 43, wherein the rinsing agent is an alcohol selected from the group consisting of methanol, ethanol, propanol, and isopropyl alcohol.

46. The process to manufacture an additive for hydrocarbon fuels as recited in claim 45, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

47. The process to manufacture an additive for hydrocarbon fuels as recited in claim 45, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

48. The process to manufacture an additive for hydrocarbon fuels as recited in claim 47, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

49. The process to manufacture an additive for hydrocarbon fuels as recited in claim 43, further comprising rinsing said powdered elemental iron with water after said powdered elemental iron has been washed with said activating acid but before said powdered elemental iron has been rinsed with said rinsing agent.

50. The process to manufacture an additive for hydrocarbon fuels as recited in claim 49, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

51. The process to manufacture an additive for hydrocarbon fuels as recited in claim 49, wherein the rinsing agent is an alcohol selected from the group consisting of methanol, ethanol, propanol, and isopropyl alcohol.

52. The process to manufacture an additive for hydrocarbon fuels as recited in claim 51, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

53. The process to manufacture an additive for hydrocarbon fuels as recited in claim 51, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

54. The process to manufacture an additive for hydrocarbon fuels as recited in claim 53, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

55. The process to manufacture an additive for hydrocarbon fuels as recited in claim 43, wherein the rinsing agent is water.

56. The process to manufacture an additive for hydrocarbon fuels as recited in claim 55, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

57. The process to manufacture an additive for hydrocarbon fuels as recited in claim 55, wherein the activating acid is an acid selected from the group consisting of hydrochloric, formic, acetic, propionic, chloroacetic, succinic, perchloric, oxalic, malonic, glutaric, adipic, maleic, citric, glycolic, diglycolic, sulfamic, butyric, trifluoroacetic, acrylic, methacrylic, crotonic, ethylenediamine tetraacetic, diethylenetriamine pentaacetic, and senecioic acids.

58. The process to manufacture an additive for hydrocarbon fuels as recited in claim 57, further comprising:

combining hydroquinone with said washed and rinsed powdered elemental iron, said picric acid, said toluene, and said isopropyl alcohol; and agitating said powdered elemental iron, said picric acid, said toluene, and said isopropyl alcohol during and subsequent to said combining.

* * * * *